(12) United States Patent
Rossback et al.

(10) Patent No.: US 7,601,140 B2
(45) Date of Patent: Oct. 13, 2009

(54) SYRINGE PRESSURE APPLICATOR

(75) Inventors: Richard A. Rossback, Irvine, CA (US); Mark C. Tsai, Ladera Ranch, CA (US)

(73) Assignee: Alcon, Inc., Hunenburg (CH)

( * ) Notice: Subject to any disclaimer, the term of this patent is extended or adjusted under 35 U.S.C. 154(b) by 754 days.

(21) Appl. No.: 10/877,193

(22) Filed: Jun. 25, 2004

(65) Prior Publication Data
US 2005/0288625 A1    Dec. 29, 2005

(51) Int. Cl.
*A61M 5/00*   (2006.01)
*A61M 5/315*  (2006.01)

(52) U.S. Cl. .................. 604/227; 604/234; 604/220

(58) Field of Classification Search ......... 604/181–243, 604/82–92, 110; 128/919; 600/5
See application file for complete search history.

(56) References Cited

U.S. PATENT DOCUMENTS

| | | | |
|---|---|---|---|
| 609,982 A | 8/1898 | Winchester | |
| 1,012,700 A | 12/1911 | Payne | |
| 1,157,552 A | 10/1915 | Kispert | |
| 1,747,243 A * | 2/1930 | Hoskins | 604/233 |
| 2,020,111 A | 11/1935 | Eisele | |
| 2,806,473 A | 9/1957 | Lingley | |
| 3,076,455 A | 2/1963 | McConnaughey et al. | |
| 3,583,399 A | 6/1971 | Ritsky | |
| 3,811,441 A | 5/1974 | Sarnoff | |
| 3,895,633 A | 7/1975 | Bartner et al. | |
| 4,112,945 A | 9/1978 | Helixon et al. | |
| 4,122,836 A * | 10/1978 | Burnett | 600/5 |
| 4,312,343 A | 1/1982 | Leveen et al. | |
| 4,540,405 A | 9/1985 | Miller et al. | |
| 4,592,746 A | 6/1986 | Burkholder et al. | |
| 4,610,672 A * | 9/1986 | Ewalt et al. | 604/220 |
| 4,642,103 A | 2/1987 | Gettig et al. | |
| 4,901,963 A * | 2/1990 | Yoder | 24/489 |
| 4,994,045 A | 2/1991 | Ranford | |
| 5,019,037 A | 5/1991 | Wang et al. | |
| 5,037,384 A | 8/1991 | Chang | |
| 5,360,409 A | 11/1994 | Boyd, III et al. | |
| 5,419,775 A | 5/1995 | Haffner et al. | |
| 5,828,073 A | 10/1998 | Zhu et al. | |
| 5,876,379 A | 3/1999 | Beauvais et al. | |
| 6,296,625 B1 * | 10/2001 | Vetter et al. | 604/227 |

(Continued)

FOREIGN PATENT DOCUMENTS

EP     0 845 275     6/1998

(Continued)

OTHER PUBLICATIONS

European Search Report—EP 1609496 (2 pages).

*Primary Examiner*—Matthew F Desanto
(74) *Attorney, Agent, or Firm*—Russell Henrichs

(57) ABSTRACT

A relatively stiff syringe pressure applicator having a pair of ears, the ears are overmolded with a relatively soft elastomer. A port extends through the syringe pressure applicator and is connected to friction fittings on either side of the pressure applicator. The external fitting is suitable for connecting to a source of pressurized air. The other fitting is sized and shaped to receive an elastomeric seal that may be inserted into the open end of a syringe to seal the syringe air tight.

18 Claims, 3 Drawing Sheets

U.S. PATENT DOCUMENTS

| | | | |
|---|---|---|---|
| 6,569,127 B1 * | 5/2003 | Fago et al. | 604/218 |
| 6,936,033 B2 * | 8/2005 | McIntosh et al. | 604/191 |
| 2003/0169898 A1 * | 9/2003 | Arasawa | 381/383 |
| 2004/0122367 A1 | 6/2004 | Sculati | |

FOREIGN PATENT DOCUMENTS

| | | |
|---|---|---|
| EP | 0 980 276 | 10/2002 |
| FR | 507 765 | 9/1920 |
| WO | WO 88/09679 | 12/1988 |
| WO | WO 94/07551 | 4/1994 |
| WO | WO 99/37344 | 7/1999 |
| WO | WO 03/094992 | 11/2003 |

* cited by examiner

SYRINGE PRESSURE APPLICATOR

BACKGROUND OF THE INVENTION

This invention relates generally to the field of syringes and, more particularly, to syringes used with viscoelastic agents.

During surgery, particularly ophthalmic surgery, various viscoelastic agents may be introduced into the surgical site. These agents generally are expressed into the surgical site out of a syringe and through a relatively thin cannula. The pressures exerted on the syringe to express the viscoelastic agent can be very high due to the high viscosity of the viscoelastic agents. Glass syringes have relatively small, fragile finger flanges. As a result of this combination of high expression forces and fragile flange, syringes used with viscoelastic have a tendency to break. Prior art syringes intended for use with viscoelastic agents, such as described in U.S. Pat. No. 4,540,405 (Miller, et al.) and U.S. Pat. No. 5,876,379 (Beauvais, et al.), have provided a flange extender that provides a better grip on the relatively small syringe so that sufficient force can be applied to express the viscoelastic agent without breaking the syringe. Recently, however, the use of pressurized air to express the viscoelastic agent from the syringe rather than manual activation of a plunger has become popular. These prior art syringe flange extenders do not provide a connection for a pressurized air source.

Accordingly, a need continues to exist for an automated means of delivering viscous materials from glass syringes by providing a connection to a source of pressurized air for expression of the viscous material.

BRIEF SUMMARY OF THE INVENTION

The present invention improves upon the prior art syringe flange extenders by providing a relatively stiff syringe pressure applicator having a pair of ears, the ears are overmolded with a relatively soft elastomer. A port extends through the syringe pressure applicator and is connected to friction fittings on either side of the syringe pressure applicator. The external fitting is suitable for connecting to a source of pressurized air. The other, internal fitting is sized and shaped to receive a elastomeric seal that may be inserted into the open end of a syringe to seal the syringe air tight.

Accordingly, one objective of the present invention is to provide a syringe pressure applicator providing a connection for a source of pressurized air.

Another objective of the present invention is to provide a relatively stiff syringe pressure applicator having a pair of ears, the ears being overmolded with a relatively soft elastomer.

Another objective of the present invention is to provide a relatively stiff syringe pressure applicator having a port extending therethrough.

This and other advantages and objectives of the present invention will become apparent from the detailed description and claims that follow.

DETAILED DESCRIPTION OF THE INVENTION

Figure 1:
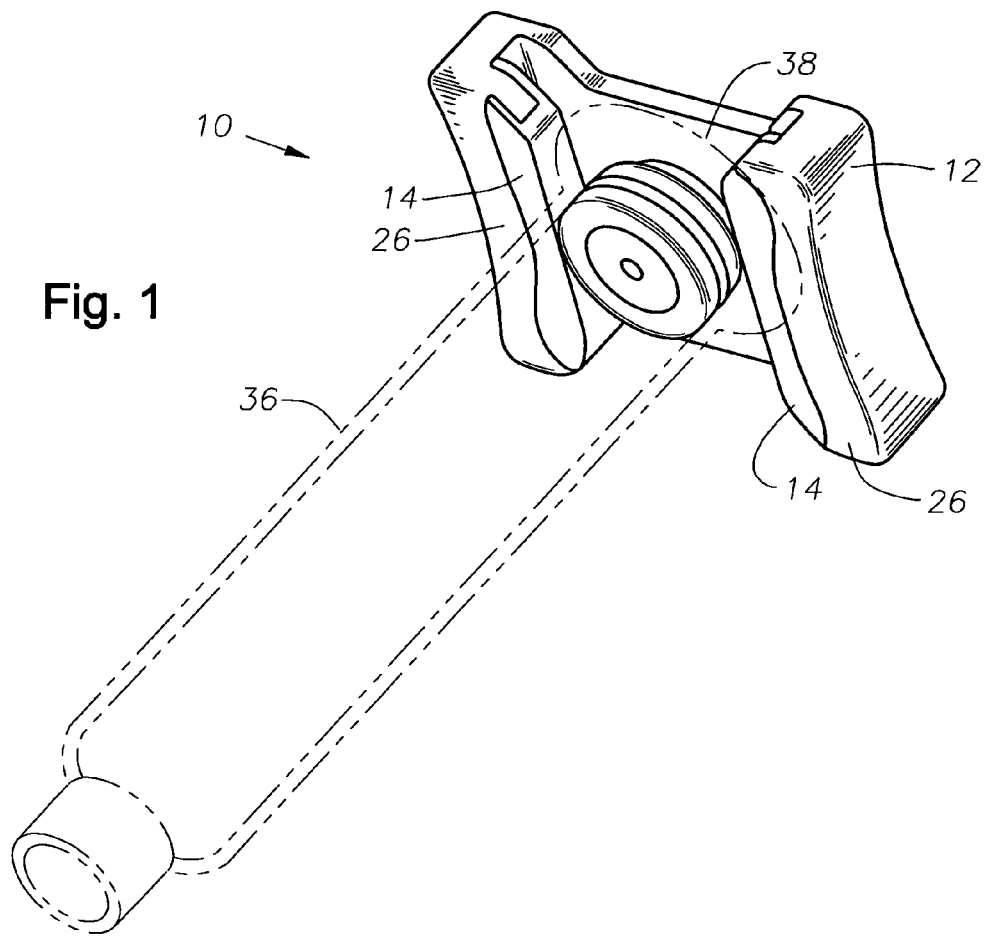
FIG. 1 is an enlarged perspective view of the syringe pressure applicator of the present invention showing a syringe in phantom.
Figure 2:
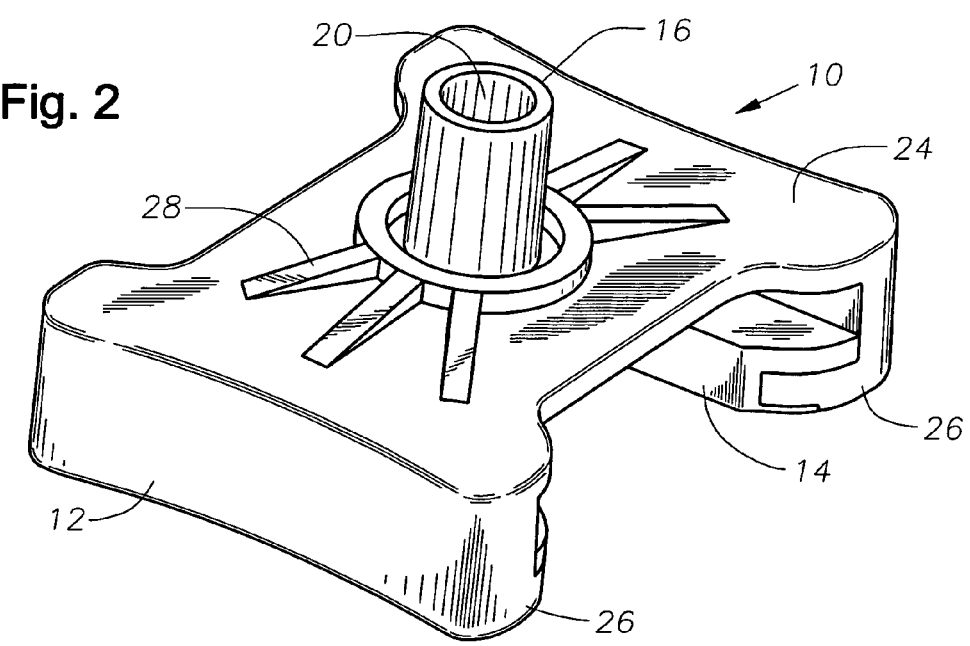
FIG. 2 is an enlarged top, left side perspective view of the syringe pressure applicator of the present invention.
Figure 3:
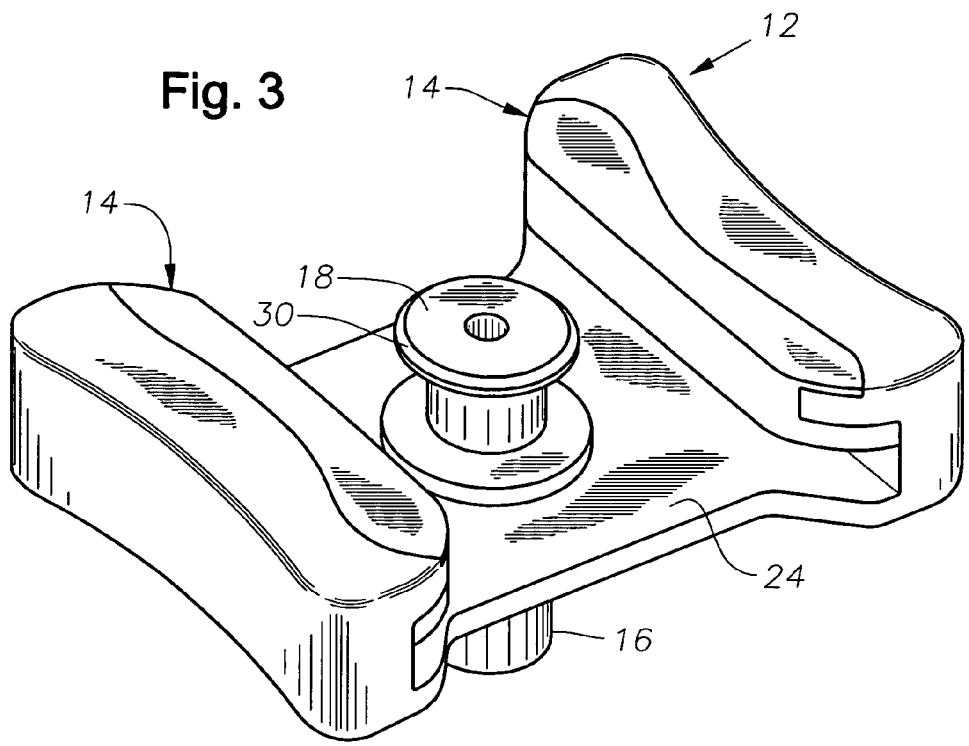
FIG. 3 is an enlarged bottom, left side perspective view of the syringe pressure applicator of the present invention.
Figure 4:
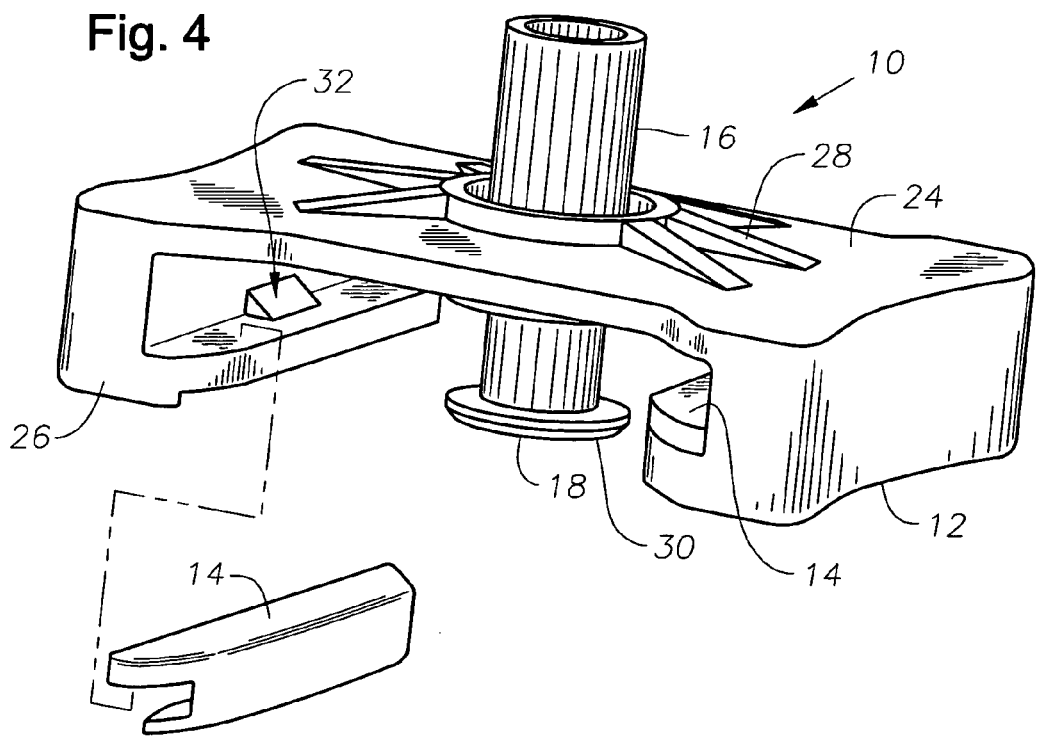
FIG. 4 is an expanded and enlarged front, right side perspective view of the syringe pressure applicator of the present invention.
Figure 5:
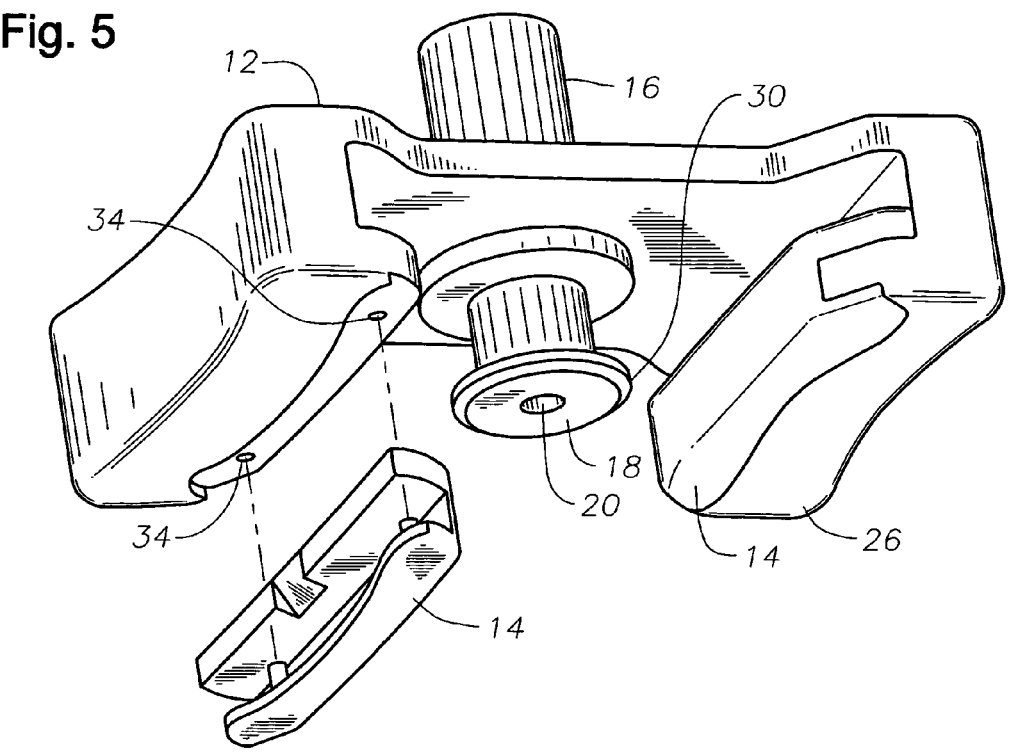
FIG. 5 is an expanded and enlarged bottom, left side perspective view of the syringe pressure applicator of the present invention.
Figure 6:
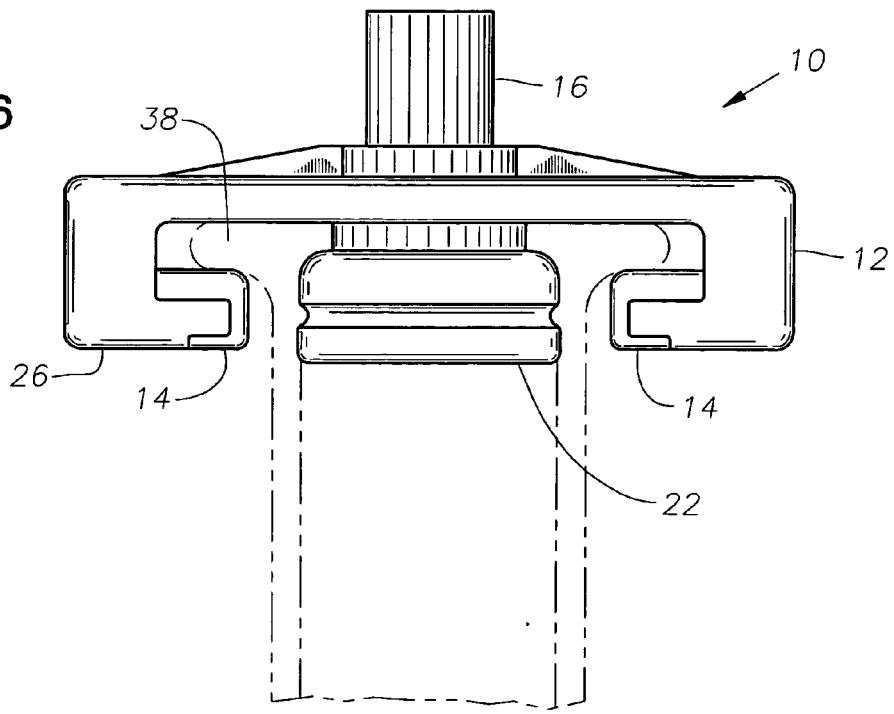
FIG. 6 is a front side view of the syringe pressure applicator of the present invention, showing the syringe pressure applicator installed on a syringe, the syringe shown in phantom.

As best seen in FIGS. 2 through 6, syringe pressure applicator 10 of the present invention generally includes body or substrate 12, pads 14, external fitting 16, internal fitting 18, bore 20 and seal 22. Body 12 preferably is molded from a relatively stiff thermoplastic material such as polycarbonate and has flat portion 24 connection to opposite, generally U-shaped ears 26. Flat portion 24 may contain stiffening ribs 28, while ears 26 may contain stiffening gussets 32 and overmold retaining holes 34. Projecting outwardly from flat portion 24 is fitting 16 on one side and fitting 18 on the other side. External fitting 16 generally is smooth and suitable for connection to a pressurized air tubing while internal fitting 18 contains retaining barb 30 that assists in retaining seal 22. Bore 20 extends all the way through flat portion 24 of body 12, external fitting 16 and internal fitting 18. Pads 14 preferably are overmolded onto at least a portion of ears 26 on body 12 by conventional overmolding techniques from a relatively soft thermoplastic elastomer, such as that sold by GLS Corporation under the trademark VERSAFLEX®. During the overmolding process, material flows into overmold retaining holes 34, thereby retaining pads 14 on ears 26. In addition, gussets 32 help prevent sliding of pads 14 on ears 26.

As best seen in FIG. 1, syringe 36 generally contains elongated or oval flange 38. Syringe pressure applicator 10 is installed on syringe 36 by placing the narrow width of flange 38 between ears 26 of body 12 so that seal 22 penetrates into the open end of syringe 36, thereby sealing the open end of syringe 36. Rotation of syringe pressure applicator 10 causes flange 38 to be captured between ears 26 and flat portion 24 while the open end of syringe 36 remains sealed by seal 22. Pressurized air may then be introduced into syringe 36 though external fitting 16, bore 20 and internal fitting 18. The use of relatively wide, flat portion 24 and ears 26, along with relatively soft pads 14, helps to spread any pressure load evenly across flange 38, thereby helping to prevent damage to flange 38 when syringe 36 is pressurized. Pads 14 also help to accommodate any irregularies in flange 38 that may form stress points.

This description is given for purposes of illustration and explanation. It will be apparent to those skilled in the relevant art that modifications may be made to the invention as herein described without departing from its scope or spirit.

We claim:

1. A syringe pressure applicator, comprising:
  a) a body having a flat portion connecting two generally U-shaped ears, an internal fitting extending outwardly from the flat portion in a first direction and an external fitting extending outwardly from the flat portion in a second direction generally opposite the first direction, the internal fitting in fluid communication with the external fitting through a bore; and
  b) a pair of pads, comprising a first pad and a second pad, wherein the first pad extends around at least a portion of a first ear of the two generally U-shaped ears, and wherein the second pad extends around at least a portion of a second ear of the two generally U-shaped ears.

2. The syringe pressure applicator of claim 1, wherein at least one of the pair of pads and at least one of the U-shaped ears comprise complementary features for coupling the at least one of the pair of pads and the at least one of the U-shaped ears.

3. The syringe pressure applicator of claim 2, wherein the complementary features include an indentation and a corresponding depression.

4. The syringe pressure applicator of claim 1 further comprising a seal held in place between the ears by the internal fitting.

5. The syringe pressure applicator of claim 1 wherein the pads are overmolded onto the ears.

6. The syringe pressure applicator of claim 1 wherein the internal fitting further comprises a barb for retaining a seal.

7. The syringe pressure applicator of claim 1 further comprising:
a pressurized air tube connected to the external fitting.

8. The syringe pressure applicator of claim 1, wherein the pads are relatively soft elastomer pads.

9. The syringe pressure applicator of claim 1, wherein the flat portion and the ears are configured to spread a pressure load evenly across a flange of a syringe and wherein the pair of pads are configured to accommodate irregularities in the flange to reduce stress points between the flange and the pressure applicator.

10. A syringe pressure applicator configured to fit to a syringe flange for application of pneumatic pressure to express a viscous material from the syringe, said applicator comprising:
a body having a flat portion connecting two opposing ears, said ears being generally U-shaped in cross section and configured to receive a syringe flange;
an internal fitting and an external fitting extending one to either side of the flat portion, the internal fitting being in fluid communication with the external fitting through a bore, wherein said internal fitting comprises a seal, configured for use to penetrate into an open end of a syringe to seal the syringe air tight, whereby rotation of the applicator over an open syringe having an elongated or oval flange causes the flange to be captured between the ears and the flat portion of the applicator, while the open end of the syringe remains sealed by the seal, and
a pair of pads made of an elastomeric material each one of which extends around at least a portion of a respective one of the two ears, configured to engage around the edge of the syringe flange.

11. The syringe pressure applicator of claim 10, wherein at least one of the pair of pads and at least one of the U-shaped ears comprise complementary features for coupling the at least one of the pair of pads and the at least one of the U-shaped ears.

12. The syringe pressure applicator of claim 11, wherein the complementary features include an indentation and a corresponding depression.

13. The syringe pressure applicator of claim 10, wherein the pressure applicator is configured to fit to a glass syringe flange.

14. The syringe pressure applicator of claim 13, wherein the flat portion and the ears are configured to spread a pressure load evenly across the syringe flange and wherein the pair of pads are configured to accommodate irregularities in the syringe flange to reduce stress points between the syringe flange and the pressure applicator.

15. The syringe pressure applicator of claim 10, wherein the seal is received by the internal fitting with a frictional fit.

16. The syringe pressure applicator of claim 10, wherein the external fitting is configured to connect to a source of compressed air.

17. The syringe pressure applicator of claim 10, wherein the body is moulded from a thermoplastic material and the pads are overmolded onto the ears.

18. The syringe pressure applicator of claim 10, wherein the internal fitting further comprises a barb for retaining a seal.

* * * * *

UNITED STATES PATENT AND TRADEMARK OFFICE
CERTIFICATE OF CORRECTION

PATENT NO. : 7,601,140 B2 Page 1 of 1
APPLICATION NO. : 10/877193
DATED : October 13, 2009
INVENTOR(S) : Rossback et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1247 days.

Signed and Sealed this

Fifth Day of October, 2010

David J. Kappos
*Director of the United States Patent and Trademark Office*